(12) United States Patent
Koewler

(10) Patent No.: US 8,647,374 B2
(45) Date of Patent: Feb. 11, 2014

(54) PATIENT TEMPERATURE CONTROL SYSTEM WITH VARIABLE GRADIENT WARMING/COOLING

(75) Inventor: Danial E. Koewler, Batavia, OH (US)

(73) Assignee: Cincinnati Sub-Zero Products, Inc., Cincinnati, OH (US)

( * ) Notice: Subject to any disclaimer, the term of this patent is extended or adjusted under 35 U.S.C. 154(b) by 1118 days.

(21) Appl. No.: 12/090,707

(22) PCT Filed: Oct. 23, 2006

(86) PCT No.: PCT/US2006/041278
§ 371 (c)(1),
(2), (4) Date: Nov. 17, 2008

(87) PCT Pub. No.: WO2007/089293
PCT Pub. Date: Aug. 9, 2007

(65) Prior Publication Data
US 2009/0240312 A1   Sep. 24, 2009

Related U.S. Application Data

(60) Provisional application No. 60/729,313, filed on Oct. 21, 2005.

(51) Int. Cl.
*A61F 7/00* (2006.01)
(52) U.S. Cl.
USPC .............................. 607/104; 607/96; 607/108
(58) Field of Classification Search
USPC ........................................... 607/96, 104, 108
See application file for complete search history.

(56) References Cited

U.S. PATENT DOCUMENTS

| 4,691,762 A | 9/1987 | Elkins et al. |
| 5,097,829 A | 3/1992 | Quisenberry |

(Continued)

FOREIGN PATENT DOCUMENTS

| WO | 9944552 | 9/1999 |
| WO | 03030790 | 4/2003 |

OTHER PUBLICATIONS

European Patent Office; Supplementary European Search Report and European Search Opinion issued in related EP Application No. EP 06849847; Dec. 30, 2010; 9 pages.

(Continued)

*Primary Examiner* — Laura Bouchelle
(74) *Attorney, Agent, or Firm* — Wood, Herron & Evans, LLP

(57) ABSTRACT

A patient temperature control system (10) uses variable temperature gradient warming/cooling in combination with a warming/cooling device (16), such as a blanket, to increase efficiency in driving a patient's temperature to a desired setpoint, with reduced occurrence of and magnitude of overshoot conditions. In operation, the controller (26) of the system (10) senses the temperature of a patient (12) via a sensor (31), for comparison to a temperature of the circulating water, sensed via sensor (30). If the patient temperature is not sufficiently close to a setpoint temperature, the system (10) is operable to warm/cool the circulating water to a temperature which differs from the patient's temperature by a temperature gradient of 10 ° C., or some other preselected initial temperature gradient. After a subsequent time interval, if the patient temperature has not moved sufficiently close to the setpoint temperature, the controller (26) incrementally raises or lowers the temperature of the circulating water, to intensify the a warming/cooling effect. This procedure repeats at desired intervals, to more efficiently reach the setpoint temperature. Thus, the system (10) is capable of automatically increasing or decreasing the temperature gradient, dependent upon subsequently sensed patient temperatures.

11 Claims, 11 Drawing Sheets

(56) References Cited

U.S. PATENT DOCUMENTS

| | | | |
|---|---|---|---|
| 5,183,039 | A | 2/1993 | Sarian et al. |
| 5,871,526 | A | 2/1999 | Gibbs et al. |
| 6,149,674 | A | 11/2000 | Borders |
| 6,188,930 | B1 | 2/2001 | Carson |
| 6,454,792 | B1 | 9/2002 | Noda et al. |
| 6,500,200 | B1 | 12/2002 | Kushnir |
| 6,508,831 | B1 | 1/2003 | Kushnir |
| 6,517,510 | B1 | 2/2003 | Stewart et al. |
| 6,551,348 | B1 * | 4/2003 | Blalock et al. ............ 607/104 |
| 6,607,517 | B1 | 8/2003 | Dae et al. |
| 6,620,187 | B2 | 9/2003 | Carson et al. |
| 6,620,189 | B1 * | 9/2003 | Machold et al. ............ 607/106 |
| 6,645,232 | B2 | 11/2003 | Carson |
| 6,660,027 | B2 | 12/2003 | Gruszecki et al. |
| 6,685,731 | B2 | 2/2004 | Kushnir et al. |
| 6,692,518 | B2 | 2/2004 | Carson |
| 6,699,267 | B2 | 3/2004 | Voorhees et al. |
| 6,799,063 | B2 | 9/2004 | Carson |
| 6,818,012 | B2 | 11/2004 | Ellingboe et al. |
| 6,827,898 | B1 | 12/2004 | Fausset et al. |
| 6,855,158 | B2 | 2/2005 | Stolpmann |
| 6,921,198 | B2 | 7/2005 | Gruszecki et al. |
| 2004/0153132 | A1 | 8/2004 | Cobb et al. |

OTHER PUBLICATIONS

Dave Riggs, TCM—New Product Development, Heart-to-Heart Newsletter, Spring 1985, Sarns Perfusion News and Information, Ann Arbor, Michigan.

Sarns Operators Manual, Temperature Control and Monitor System, Sarns, Inc., Ann Arbor, Michigan, May 1985.

Sarns Operators Manual, Temperature Control and Monitor System, Sarns, Inc., Ann Arbor, Michigan, Mar. 1985.

Sarns TCM II 3M HealthCare, Ann Arbor, Michigan, 1989.

TCM Sales History Prior to 1999.

3M Sarns TCM II, The 3M Sarns TCM II—precise temperature control at your fingertips, 3M Health Care, USA, 1994.

Sarns TCM II Operators Manual, 3M Health Care, USA, 1994.

Sarns TCM II Technical Support Manual, 3M Health Care, USA, 1995.

Deposition Transcript of Stephen Wells, Sep. 24, 2008, Ann Arbor, Michigan.

Medi-Therm III Hyper/Hypotermia Machine MTA6900 Operator's Manual, Gaymar, Sep. 2000.

Medi-Therm III Hyper/Hypothermia Machine MTA6900 Operator's Manual, Gaymar, Sep. 2000.

Caruso C, Hadley B, Shukla R. Frame P, Khoury J., Cooling Effects and Comfort of Four Cooling Blanket Temperatures In Humans With Fever, Nursing Research 1992; 68-72.

Hubbard R., Armstrong L., Young A., Rapid Hypothermia Subsequent to Oral Nicotinic Acid Ingestion And Immersion In Warm (30° C.) Water, American Journal of Emergency Medicine 1988; 6: 316-317.

Deposition Transcript of Dr. Thomas P. Stewart, Oct. 1, 2008, Ann Arbor, Michigan.

International Search Report, PCT/ISA/202, PCT/ISA/210, PCT/ISA/220.

Medivance Press Release: Medivance, Inc., Begins Market Introdcution of the Arctic Sun TM, The Next Generation Of Patient Temperature Management Systems, Denver, Jan. 28, 2002.

Medtronic Press Release: Medivance Unveils First Non-Invasive Patient Cooling System at TCT 2003 Conference, Louisville, Colorado, Sep. 15, 2003.

Kimberly-Clark Patient Warming System brochure, 2003.

Sarns, Inc., SARNS Operators Manual Temperature Control and Monitor System, Ann Arbor, Michigan, 1985.

* cited by examiner

PATIENT TEMPERATURE CONTROL SYSTEM WITH VARIABLE GRADIENT WARMING/COOLING

The present application claims priority to PCT Application No. PCT/US2006/041278, entitled "Patient Temperature Control System With. Variable Gradient Warming/Cooling," filed on Oct. 23, 2006, which in turn claims priority to U.S. Provisional Patent Application Ser. No. 60/729,313, bearing the same title and filed on Oct. 21, 2005, and which is expressly incorporated by reference herein in its entirety.

FIELD OF THE INVENTION

This invention relates to a patient temperature control system suitable for raising, lowering, or maintaining a patient's temperature through conductive heat transfer.

BACKGROUND OF THE INVENTION

To understand the present invention, it is helpful to first understand the capabilities of existing patient temperature control systems of the same type. More specifically, the assignee of this invention has marketed a patient temperature control system which uses a closed loop fluid circuit, typically with water circulating through a blanket, to conductively warm or cool a patient to a desired temperature. This temperature control system is called the Blanketrol-II system. This system provides three modes of operation, namely MANUAL CONTROL, AUTO CONTROL and MONITOR ONLY. This last mode represents use of the system solely as a patient temperature monitor. In other words, in this last mode, the system senses the patient temperature but does not circulate warming or cooling water to the patient via a blanket or other device.

In MANUAL CONTROL, this prior system raises or lowers the temperature of the circulating fluid, namely water, to a setpoint temperature. The setpoint temperature is selectable, or adjustable, by the operator, within a range of acceptable temperatures for the circulating water. In the MANUAL CONTROL mode of operation, the system warms or cools the circulating water until it reaches the setpoint temperature, regardless of the patient temperature. The control panel of the system displays the water temperature in one window, and also displays the setpoint temperature in a separate window. The operator may adjust the setpoint temperature, by using the TEMPSET push button, and the triangularly-shaped up and down indicators.

This system also displays the patient temperature when a patient temperature probe is placed so as to sense the temperature of the patient, and when the probe is operatively connected to the correct input of the controller.

However, in this MANUAL CONTROL mode the system does not use the sensed patient temperature to automatically change or effect the temperature of the circulating water.

During operation in the AUTO CONTROL mode, the operator again sets a desired setpoint temperature for the patient, using the controls. The desired setpoint temperature is displayed on the panel. In the AUTO CONTROL mode, the patient temperature is sensed, and if the sensed patient temperature is below the setpoint temperature, the system circulates warming water to the patient in order to warm the patient until the sensed patient temperature reaches the setpoint temperature.

Thus, in this mode the controls of the system compare the setpoint temperature with the sensed temperature. Once the patient has been sufficiently warmed so that the sensed patient temperature reaches the setpoint temperature (or is within an acceptable range of the setpoint temperature) the system discontinues the active warming of the circulating water, but continues to circulate the water.

Thereafter, if the patient's temperature again falls below the setpoint temperature (or outside an acceptable range including the setpoint), the temperature control system will once again actively warm the circulating water, to once again raise the patient's temperature to the setpoint temperature.

Conversely, if the initially sensed patient temperature is above the setpoint temperature, the system cools the water and circulates the cooled water in order to cool the patient down to the setpoint temperature. Once the sensed patient temperature reaches the setpoint temperature (or within an acceptable range thereof), the system discontinues cooling the circulating water, but continues to circulate the water.

In the AUTO CONTROL mode, the system initially uses the warmest water available in order to warm the patient, or the coolest water available in order to cool the patient, within reasonable and acceptable water temperature limits. Typically, the coolest water available is generally about 4° C. (40° F.), and the warmest water available is generally about 42° C. (107.5° F.).

By using the warmest or coldest water available, this system utilizes the greatest possible warming or cooling effect, in order to bring the patient's temperature to the setpoint temperature in the shortest time possible. Using the coldest or the warmest water available is the best way to quickly move the patient's temperature to the setpoint temperature, at which point the system then discontinues further warming or cooling of the circulating water.

This may cause some patient temperature discomfort. But this disadvantage is secondary to the primary goal of getting the patient's temperature to the setpoint. Thus, patient discomfort is a consideration, but not the most important consideration.

Also, in some cases this type of warming (or cooling) of the patient may cause the patient's temperature to become warmed (or cooled) beyond the setpoint. This condition is called "overshoot." Overshoot can occur because, in the AUTO CONTROL mode, the system continues to warm or cool the circulating water until the sensed patient temperature reaches the setpoint temperature. Thereafter, the system discontinues further warming or cooling. But at the time heating or cooling is discontinued, the circulating water remains relatively warmed or relatively cooled for some transition time thereafter. The liquid in this closed liquid circuit cannot be immediately switched from hot to cold, or vice versa. Such temperature transitions take some time, depending on the total volume of the water, and the efficiency of the heat transfer. As a result, the circulating water continues to warn or cool the patient, sometimes beyond the setpoint temperature, such that it becomes necessary thereafter to cool (warm) the patient in order to get the patient back to the setpoint temperature. This means that the system may automatically swing back and forth between circulating warning water and then circulating cooling water to the same patient, or vice versa, depending upon the successively sensed patient temperatures.

When overshoot occurs, the system switches from warming to cooling, or from cooling to warming, but again with the warmest or coolest water available. This can sometimes result in several overshoots, thereby requiring the system to successively switch back and forth from warmest water to coolest water, or vice versa. Eventually, the patient's temperature becomes stabilized at or about the setpoint temperature. However, in some cases a subsequent fluctuation of the patient's temperature from the setpoint temperature may cause one or more subsequent overshoots. These overshoot situations occur, at least in part, because the temperature gradient between the setpoint temperature and the warmest water available, or the coolest water available, can be relatively high.

In the past, others have sought to minimize patient discomfort by using water warmed or cooled to a predetermined temperature gradient, rather than the warmest or coolest water available. For example, the 1985 SARNS Operating Manual describes a temperature control and monitor unit, primarily for supplying temperature controlled water to a blood heat exchanger in an extracorporeal circuit. The SARNS Manual also describes a "Blanket Supply" feature, for supplying water to a blanket to externally heat or cool a patient. Within this context, the SARNS Manual discloses gradient warming, via a GRADIENT switch. This switch enables the operator to select a rewarming temperature gradient for the circulating water, namely, either 6° C. or 10° C. above the sensed patient temperature.

Thus, this SARNS Manual discloses the use of automatic gradient temperature control, namely, gradient warming, as opposed to warmest water available. Similarly, U.S. Pat. No. 6,517,510 issued to Stewart, uses essentially the same gradient temperature control strategy in its Automatic mode, namely a fixed, predetermined temperature gradient for patient warming or cooling With the predetermined gradient fixed at the factory by the designer of the machine, at one or two filxed and predetermined gradient values.

The use of automated gradient temperature control, i.e., warming or cooling, can reduce the occurrence and/or the magnitude of overshoot. That is because the selected temperature differential i.e., the temperature difference between the warming fluid (or the cooling fluid) and the sensed patient temperature, will not be as great as would occur if the warmest or the coolest water available were initially used. However, if too much emphasis is placed on avoiding temperature overshoot, the main goal of rapidly cooling (or warming) the patient may be sacrificed.

For instance, if the sensed patient temperature is 37° C. (98.6° F.), and it is desired to cool the patient to a temperature of 28.9° C. (84° F.), and the cooling water is only cooled to a temperature of 27° C. (80.5° F.) (which represents a 10° C. temperature gradient from the sensed patient temperature, common temperature gradient), the cooling water will clearly not produce the same cooling effect as cooling water which is cooled to about 4.5° C. (40° F.), as was done with the use of the coolest water available. Accordingly, in some instances, by not using the coldest available water, it may take much longer for the patient's temperature to be reduced to the setpoint temperature. In fact, the "cooling" water in this example, at a temperature of about 27° C. (80.5° F.), is actually warmer than ambient air. This means that the cooling blanket actually produces a lesser cooling effect than would occur if the patient were simply exposed to ambient air, with no blanket at all. This is one situation where the use of gradient heating or cooling, per se, suffers from a practical and common limitation.

Thus, although the use of gradient cooling or warming may reduce the occurrence and/or magnitude of overshoot, it may also sacrifice rapid and efficient cooling or warming of the patient, because it will take longer to cool or warm the patient to the setpoint temperature. In some cases, the additional time needed to cool the patient to the setpoint temperature may be significant. And as noted above, sometimes the cooling water used in gradient cooling is warmer than room temperature air. Thus, there is a tradeoff among the desires to efficiently and effectively warm or cool the patient to the desired setpoint temperature in the shortest reasonable time frame, the desire to minimize the magnitude and occurrence of temperature overshoot, and the concern for patient comfort.

It is an object of the present invention to conveniently achieve the primary goal of getting the patient's temperature to a desired setpoint, while also addressing the secondary issues of patient discomfort and overshoot.

It is another object of this invention to minimize the occurrence of overshoot, and to also reduce the magnitude and duration of any overshoot that does occur.

It is still another object of the invention to achieve the previous stated objects in a user-friendly manner, without adding undue complexity for hospital personnel.

SUMMARY OF THE INVENTION

To achieve the above-stated objects, the present invention permits the use of a variable temperature gradient for warming or cooling the patient. More specifically, the present invention allows the operator to set an initial temperature gradient, i.e. the temperature difference between the sensed patient temperature and the circulating fluid. Thereafter, during operation, the system automatically and incrementally increases or decreases the magnitude of that initially-selected gradient temperature, or leaves it the same, depending on subsequently sensed patient temperatures.

Thus, after a predetermined period of time, such as half an hour, if the difference between the patient temperature and the setpoint temperature is still too great (as may occur if the patient temperature is not dropping fast enough, because the temperature difference between the circulating water and the patient is simply not great enough), the present invention automatically increases the temperature gradient (the difference between the circulating water and the sensed patient temperature) by an amount of 5° C. For instance, if an initial temperature gradient of 10° C. has not caused the sensed patient temperature to drop to the setpoint temperature within one half hour, the controller of this system further cools the circulating water, so that the temperature differential between the sensed patient temperature and the circulating water now becomes 15° C., instead of 10° C. In this example, the system increases the magnitude of the temperature gradient, based on the subsequently sensed patient temperatures, after an initial sensed temperature.

Additionally, after yet another predetermined time increment, for instance another half hour, this control feature again compares the sensed patient temperature with the setpoint temperature, and may then either: 1) further increase the temperature gradient of the cooling water, say from 15° C. to 20° C.; or 2) retain the same temperature gradient of 15° C.; or 3) reduce the temperature gradient from 15° C. back to the initial temperature gradient of 10° C. Thus, at the next predetermined time interval, based on the sensed patient temperature, the present invention does one of the following: 1) increases the temperature gradient magnitude, by adding another increment of 5° C. to the prior gradient (if greater, or faster cooling is needed); 2) keeps the temperature gradient the same (if the rate of cooling or warming is progressing in an acceptable manner); or 3) decreases the temperature gradient by subtracting an increment of 5° C. from the prior gradient (if lesser, or slower cooling is needed). As presently configured, the magnitude of these gradient increments has been set, or fixed, at 5° C. Nonetheless, this increment could be made variable, but it is also recognized that the user-friendliness of this system is maintained by minimizing the number of operator decisions.

With this feature the system of the present invention provides greater versatility in causing the patient's temperature to move upwardly or downwardly to the desired setpoint temperature. And this system does this in a manner which quickly and efficiently drives the patient temperature in the desired direction, while thereafter automatically adjusting the temperature gradient, i.e. the difference between the sensed patient temperature and the circulating water, as needed, to increase or decrease the heating or cooling effect, as needed. Because this system automatically varies the temperature gradient, this system efficiently and effectively warms or cools the patient to the setpoint temperature in a reasonable time, while reducing the occurrence and the magnitude of overshoot. Because this system uses some of the same modes, and generally the same essential layout as the prior system, it is relatively easy to understand for the operator. That is, the operator has user-friendly access to the familiar modes of operation of the existing system, but with the added versatility and performance of these new variable temperature gradient features.

These and other features of the invention will be more readily understood in view of the drawings and the following detailed description of the drawings.

DETAILED DESCRIPTION OF THE PREFERRED
EMBODIMENT OF THE PRESENT INVENTION

Figure 1:
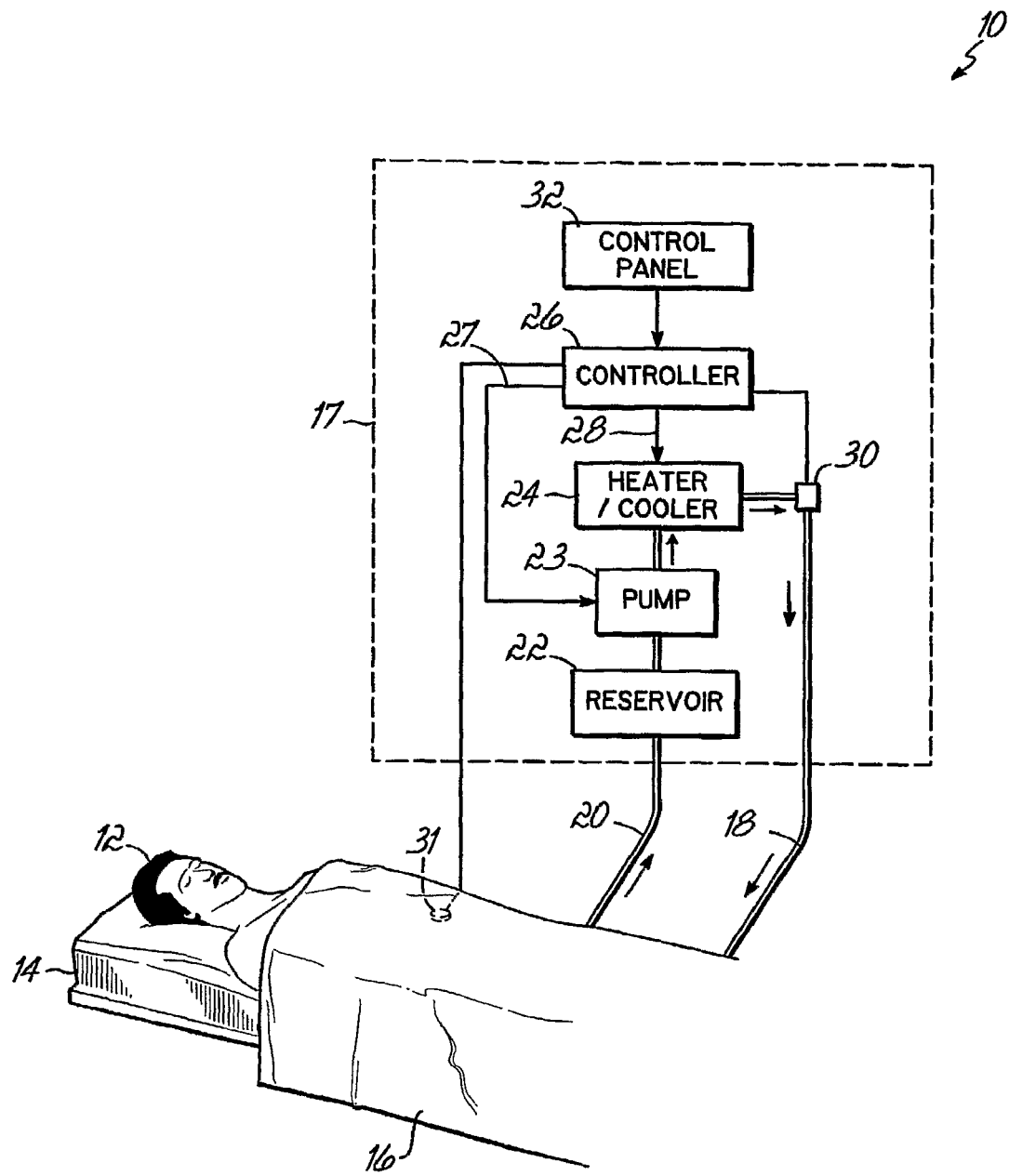
FIG. 1 is a schematic diagram which generally shows an exemplary overall arrangement for the components that may be used in the present invention.

As noted above, FIG. 1 shows a schematic layout of a patient temperature control system 10 in accordance with the invention. This layout is meant to supply the proper background and context for explaining the operational capability of the present invention. It is not meant to be limiting in scope. More particularly, FIG. 1 shows a patient 12 supported on a table 14, with a warming/cooling device, in this case a blanket 16, substantially covering the patient 12. Water flow lines interconnect the blanket 16 with a housing, shown by a dash line 17. More particularly, FIG. 1 shows an inflow conduit line 18 which routes circulating water to the blanket 16, and an outflow line 20 which routes the circulating water back to the housing 17. Additional fluid lines could be used, if desired.

Within housing 17, water from the outflow line 20 flows to a reservoir 22. From the reservoir 22, the circulating water flows to a pump 23, then through a heating/cooling device designated generally by reference numeral 24, and then outwardly again from the housing 17. The focus of the invention is not on the particular details of the circulating water components residing within the housing 17, such as the reservoir 22, the pump 23, or the heating/cooling device 24. Rather these components are shown generally in block form, for schematic purposes.

A controller 26 resides within the housing 17. The controller 26 operatively connects to the heating/cooling device 24 via an electrical connector 27, and also to the pump 23 via an electrical connector 28. The controller 26 connects to a first temperature sensor 30 which senses the circulating water temperature as it exits the heating/cooling device 24, and also a second temperature sensor 31 which senses the body temperature of the patient 12. As with the circulating water components, the electrical connectors which connect to the components residing within housing 17 and with the temperature sensors 30 and 31 are merely shown in schematic form, to illustrate the general layout of the present invention. The controller 26 operatively connects to a control panel 32. An operator selectively controls operation of the system 10 via push button controls shown on the control panel 32. Stated another way, the controller 26 is microprocessor-based and configured to control warming and/or cooling in a manner which cooperates with the control panel 32 via the push buttons which are shown best in FIG. 2.

Via the control panel 32, the present invention achieves one or more of the above-stated objects by more specifically controlling the temperature of the circulating water relative to the sensed patient temperature and the setpoint temperature. Notably, the present invention continues to use the same general layout of the controls as the assignee's prior Blanketrol-II system. That is, the indicator windows remain generally in the same relative positions, and the TEMPSET controls for the setpoint temperature remain centered. That is, a display window 35 shows the setpoint temperature. Display windows 41 and 45 show the temperature of the circulating water and the patient temperature, respectively. This temperature can be changed by depressing the TEMP SET push button 36, and then either the raise 37 or lower 38 buttons. Also, in the present invention the MANUAL CONTROL button 42 and the MONITOR ONLY button 43 represent operational modes that remain identical to those of the pre-existing Blanketrol-II system.

The main operational advantages of the present invention relate primarily to options that are shown in the right side of control panel 32, below the AUTO CONTROL button 46, namely features which enable variability of the temperature gradient of the circulating water. Due to these features, the present invention has greater capability for more specific control over the temperature of the circulating water relative to the sensed temperature of the patient and the setpoint temperature, compared to systems that always use the warmest water available or the coolest water available for warming or cooling, respectively. At the same time, the present invention still allows the operator to use the warmest water available or the coldest available water, if that option is desired. For all of these reasons, the present invention remains user-friendly for the operator and cost-effective for the institution, and represents a better procedure for efficiently and economically driving a patient's body temperature to a desired setpoint.

In the AUTO CONTROL mode, the system 10 works in the same manner as the prior Blanketrol II system. That is, it uses the warmest or coolest water available.

Via pushbutton 48, the system 10 provides an option designated as GRADIENT 10° C., which involves circulating warming or cooling water which is warmed or cooled at a temperature which is, at a maximum, 10° C. different from the sensed patient temperature. Stated another way, the present invention uses temperature gradient warming or cooling (i.e. gradient warning, or gradient cooling), wherein the temperature gradient reflects a 10° C. difference between the temperature of the heating or cooling water and the sensed temperature of the patient.

Additionally, the operator can also choose to set the temperature gradient at a desired magnitude which differs from 10° C. This is done by selecting an option designated as GRADIENT VARIABLE, via the appropriately labeled control button 50. Thus, the present invention provides for operator selectability of the temperature gradient, to apply temperature gradients other than merely 10° C.

As with the prior Blanketrol II system, the AUTO CONTROL push button 46 is pushed after the operator uses the TEMP SET push button 36 and the incremental push buttons 37 and 38, to determine the target temperature for the circulating fluid. This sequence is also true for the GRADIENT 10° C. and the GRADIENT VARIABLE modes. That is, the operator first sets the target temperature. In GRADIENT VARIABLE mode, after push button 50 is pushed, the operator again uses the TEMP SET button 36 and the increment push buttons 37 and 38 to select a desired temperature gradient. As described up to this point, the system 10 maintains the predetermined temperature gradient, either 10° C. or a different value, for the duration of the patient cooling or warming.

Compared to the prior systems which only used the warmest or the coolest water available, the present invention is capable of also circulating warming or cooling water which is warmed or cooled at a temperature that differs from the sensed patient temperature by, at a maximum, a differential of 10° C. (by selecting the Gradient 10° C. option) or some other preselected differential (by selecting the GRADIENT VARIABLE option). Generally, for the system 10, the hardware and software components may be the same or updated versions of corresponding components of the Blanketrol-II system.

The controller 26 cooperates with the temperature sensor for the patient 31 and the temperature sensor 30 for the circulating fluid 30, an internal timer, and the warming/cooling device 24 within the housing 17. The system 10 coordinates the interaction of these components in a manner dictated by the control push buttons shown in FIG. 2. The operational control of the system 10 can best be understood by describing the various options for the functional operation of the system 10, with reference to FIGS. 3A-3I. More specifically, FIGS. 3A-3I show, in graphical format, the sensed patient temperature, the setpoint temperature, the ambient temperature, and the temperature of the circulating water. All of these parameters are shown by lines which extend across the graph. These time versus temperature graphs schematically illustrate the operational details of the system 10, and how those details vary in the different modes of operation. In each graph, time is depicted on the horizontal axis, and temperature is depicted on the vertical axis, in degrees centigrade. Generally, the graphs depict a temperature range from 3° C. to 43° C., which is roughly equivalent to about and 37½° F. to about a 109½° F. The time measurements are shown in military fashion (with hours, minutes and seconds shown as: hh:mm:ss). Some of the time scales differ from graph to graph. These graphs are computer generated. They do not represent actual tests. Nonetheless, applicant believes that the graphs accurately reflect the operational capability of the present invention.

Manual Mode

Figure 3A:
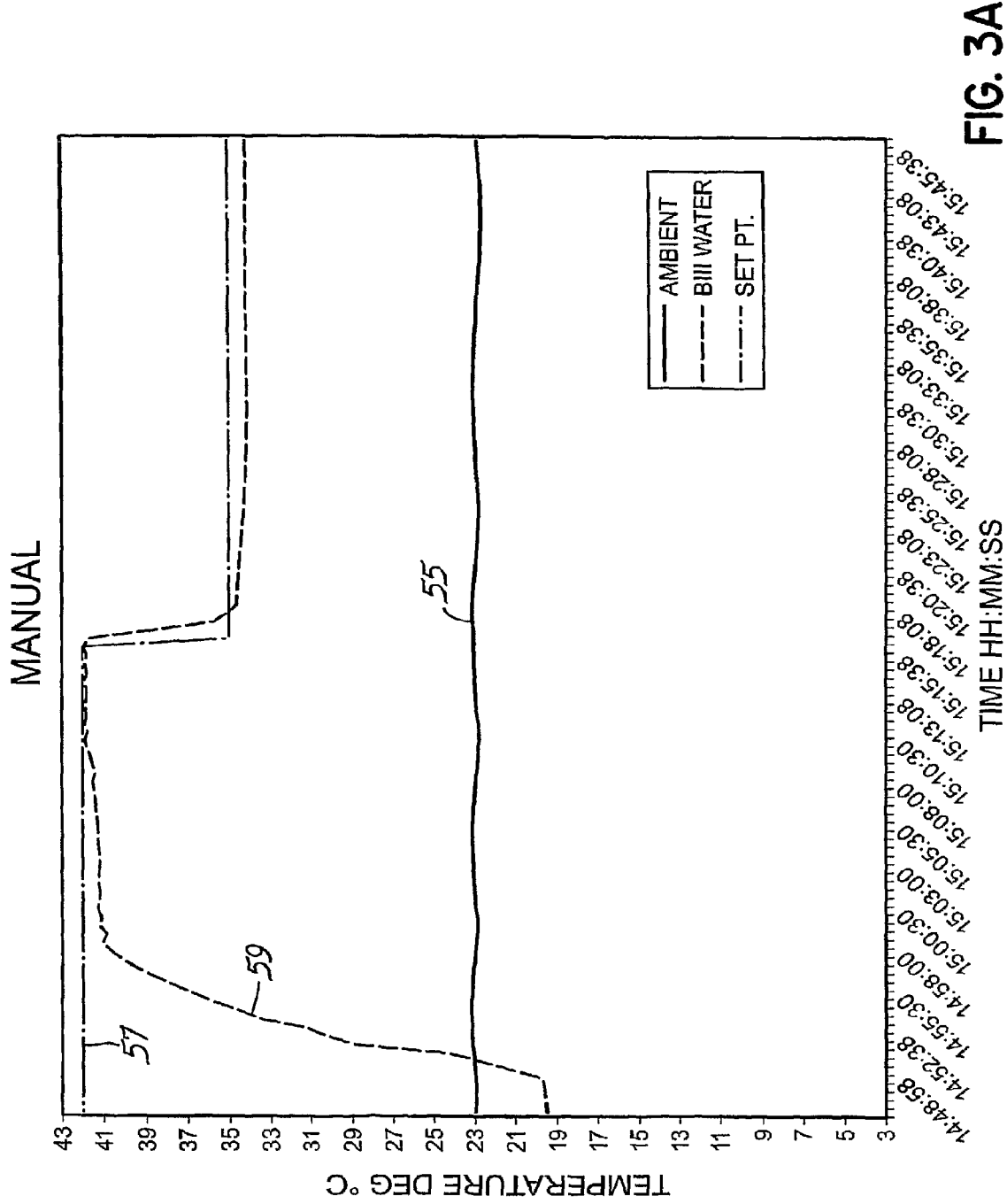
FIGS. 3A-3I are graphs which show temperature versus time, with time on the horizontal axis and temperature on the vertical axis, for the setpoint temperature, the circulating water temperature, the sensed patient temperature, and ambient temperature. These graphs illustrate the operational capability of the present invention, in accordance with a preferred embodiment thereof.

FIG. 3A shows that the controller 26 controls the circulating water temperature so as to track, or follow, the setpoint temperature during operation in the Manual mode. Ambient temperature is shown by solid dark line 55, which extends horizontally across the graph at about 23° C. The setpoint temperature is shown by hashed line 57. The circulating water temperature is shown by dotted line 59. At the left side of the graph, hashed line 57 shows that the setpoint temperature is at about 42° C., while the circulating water temperature (dotted line 59), is about 19.5° C. This graph shows that when the controller 26 heats the circulating water, the temperature of the circulating water raises to the setpoint temperature, until the circulating water temperature eventually levels off. If the setpoint temperature is reduced, as shown at about half way across the graph, and in this case to a temperature of about 35° C., the controller 26 cools the circulating water until it reaches the setpoint temperature.

This manual mode of operation for the system 10 is identical to the manual mode of operation for the prior Blanketrol-II system. It is described herein primarily because a visual depiction of this manual mode of operation helps to clarify the other visual depictions of the variable gradient temperature modes of operation for the system 10. In the manual mode, the patient's temperature may be sensed, but it is not automatically controlled in coordination with the temperature of the circulating water. Instead, the operator must closely monitor patient temperature and the circulating water temperature, and use the setpoint temperature accordingly.

Auto Mode

Figure 3B:
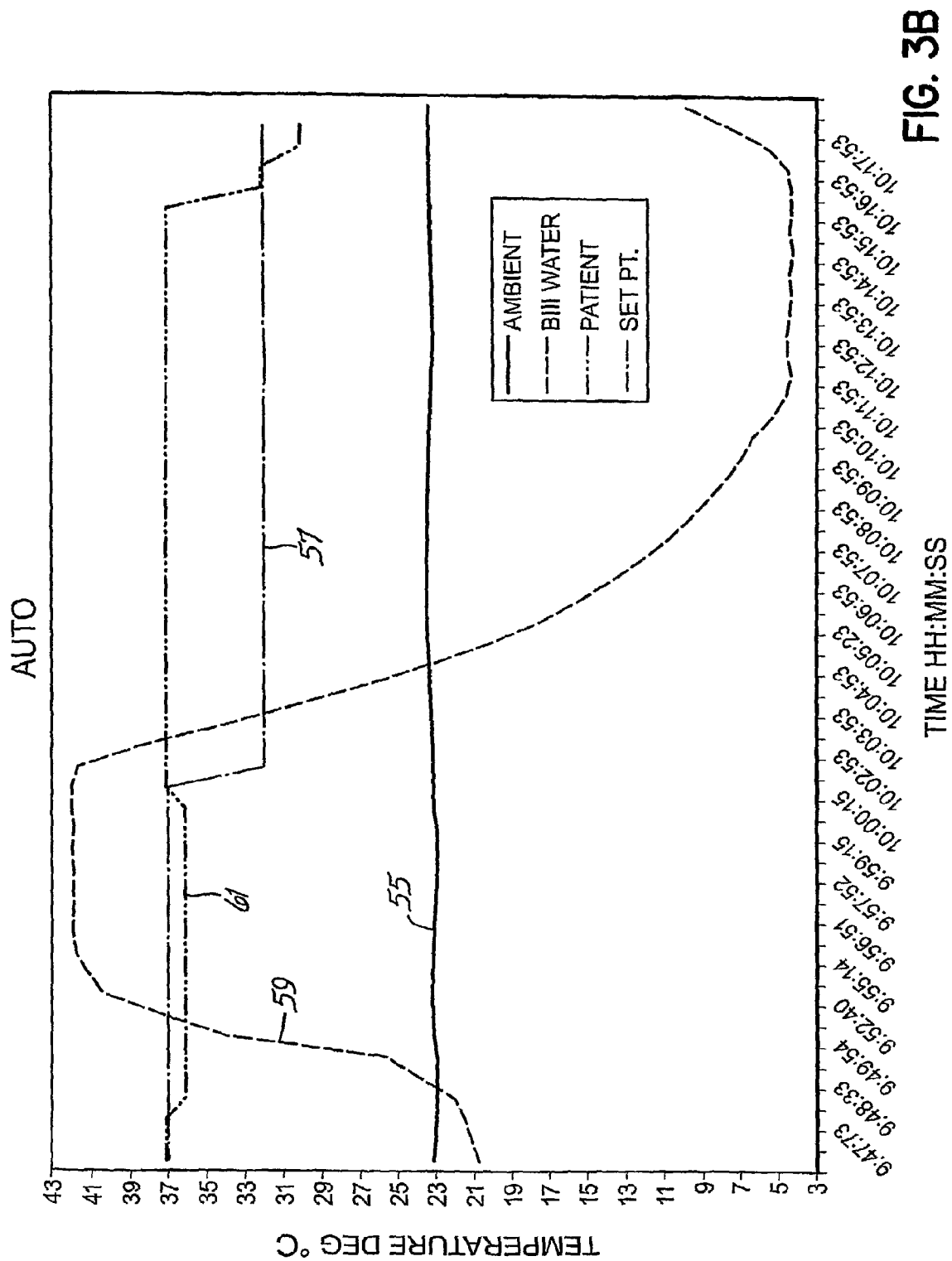

FIG. 3B shows the Auto mode. This is represented by the AUTO CONTROL push button 46, and no additional push buttons. In this mode, the system 10 uses the warmest water available and the coldest water available, within recognized safety restrictions. As with the Manual mode (FIG. 3A), this mode is the same as the prior Blanketrol-II system.

The ambient temperature is shown as a solid line 55. The setpoint temperature is shown by hashed line 57, and is initially set at 37° C., but then subsequently reduced to 32° C. The circulating water is shown as dotted line 59, and starts at 21° C. The patient temperature is shown by the hybrid dashed/dotted line 61, and is initially 37° C.

In this mode, the system 10 senses the patient's temperature via sensor 31, and the circulating water temperature via sensor 30, and compares them to the setpoint. Initially, the temperature of the circulating water increases in the direction of ambient temperature, and toward the higher patient temperature. When the patient temperature moves downwardly from 37° C. to 36° C., at 9:48:33, the controller 26 begins to actively warm the circulating water, thereby causing the circulating water to reach a temperature of about 42° C., which occurs at 9:56:51. At this point, the controller 26 discontinues further warming, for safety reasons, due to a temperature override. Eventually, at the time of 10:00:15, the patient's temperature raises back up to the setpoint temperature, as a result of the warmed circulating water.

At that point, when the setpoint is lowered by 5° C., to 32° C., the system 10 begins cooling the circulating water with the coolest water available, eventually reducing the temperature of the circulating water to 4° C., as shown by the line 59. Eventually, the cooling effect of the circulating water causes the patient's temperature to drop back down to the last setpoint, to 32° C. This is shown on the far right side of the graph.

Thereafter, the graph shows the patient's temperature continuing to decrease below the setpoint temperature. At that point, the controller begins to warm the circulating water in order to drive the patient's temperature back up to the setpoint.

FIG. 3B shows some wide swings for the temperature of the circulating water. For instance, starting at about 10:11:53, the circulating water is at the lowest temperature available, which is 4° C. This graph also shows, at the very far right side, a condition of overshoot. That is, the use of the coldest water available for cooling the patient has caused the patient's temperature to decrease downwardly, first to the setpoint temperature, and then down to a point below the setpoint temperature. Thus, the use of the coolest water available has caused an "overshoot" condition.

Gradient 10° C. and Gradient Variable

Figure 3C:
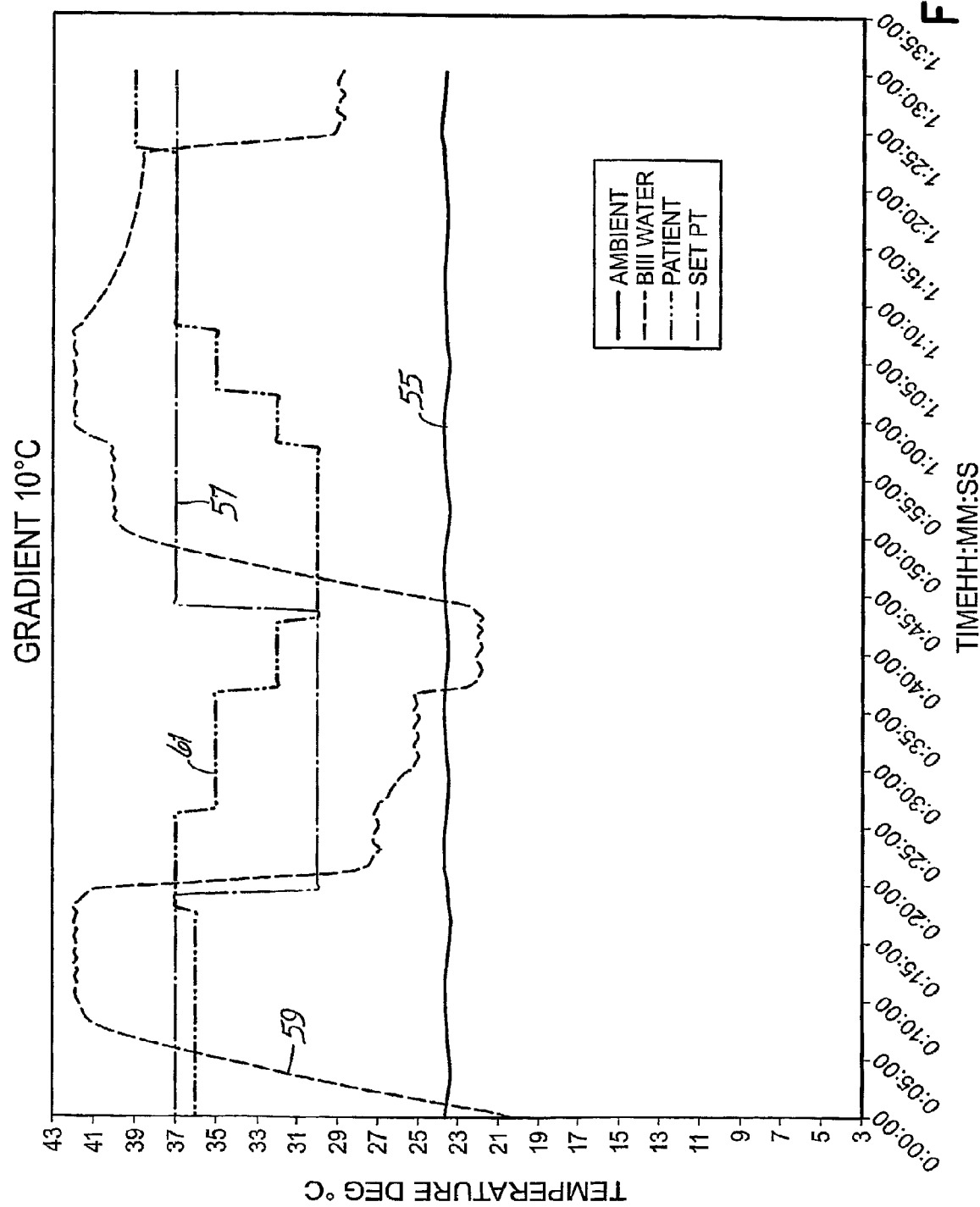
Figure 3D:
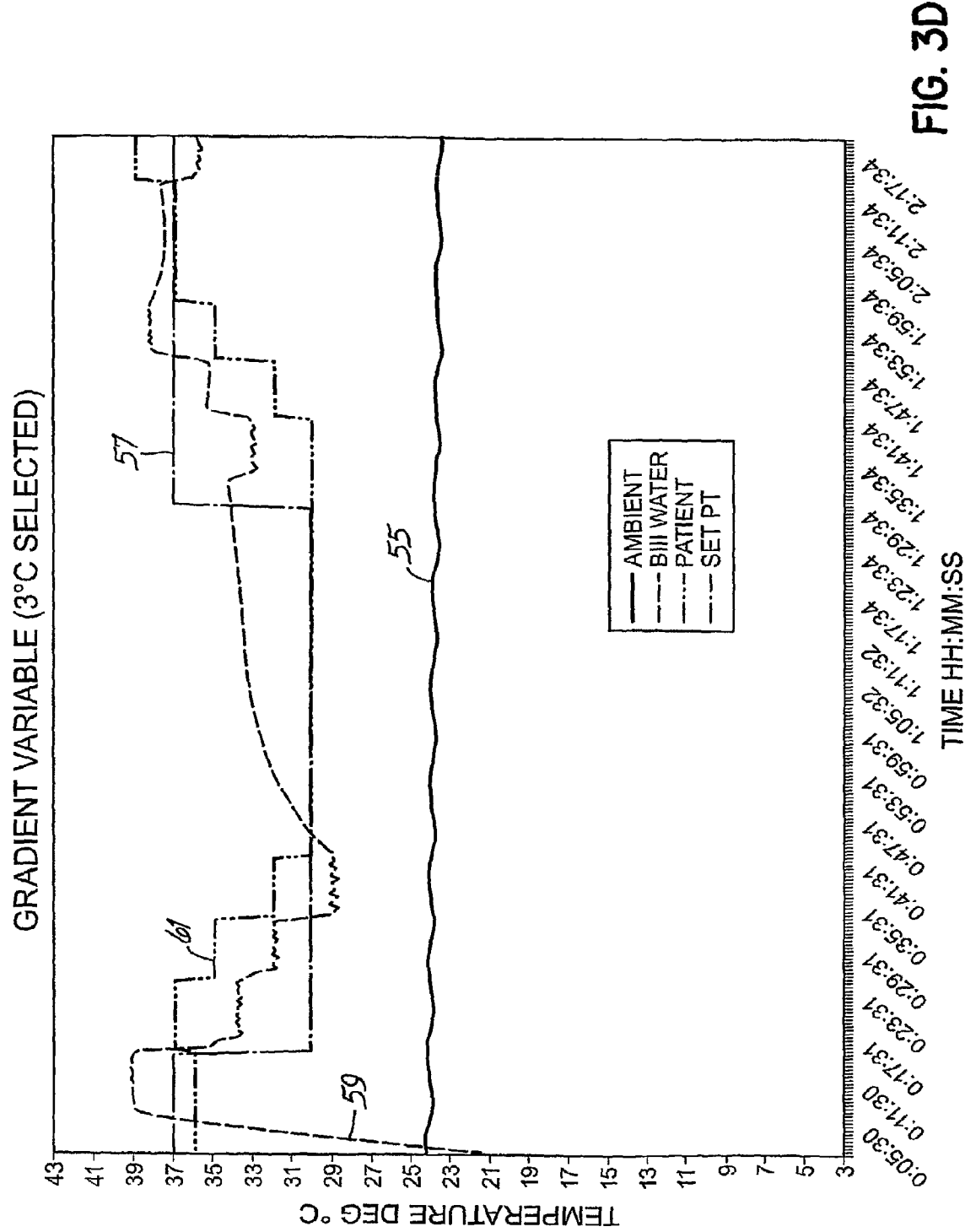

FIGS. 3C and 3D generally depict gradient warming and gradient cooling using a temperature gradient of 10° C. (FIG. 3C) and a selected temperature gradient of 3° C. (FIG. 3D). In both graphs, the ambient temperature is shown as a solid line 55 at 23° C. The circulating water is shown by dotted line 59, and the sensed patient temperature is shown by hybrid line 61. The setpoint temperature is shown by dashed line 57.

FIG. 3C shows the patient temperature (36° C.) initially below the setpoint temperature (37° C.). In this condition, the controller 26 warms the water at a temperature that is, at a maximum, predetermined temperature gradient above the sensed patient temperature. In this case, that predetermined temperature gradient is 10° C. However, for safety reasons the system 10 limits temperature of the circulating water to 42° C., due to an overheat override, as is known. For some time thereafter, the temperature of the circulating water and the patient temperature remain generally parallel, as the system 10 gradiently warms the patient.

Eventually, just before the 0:20:00 mark, the setpoint temperature decreases from 37° C. to 30° C. Correspondingly, after the system 10 senses the patient temperature well above the setpoint temperature, the controller decreases the temperature of the circulating water toward a temperature of 27° C., or 10° below the sensed patient temperature of 37° C.

This next section of the graph shows a step-like decrease of the patient temperature (in three steps) as a result of gradient cooling, with the circulating water also correspondingly decreasing in step-like fashion so as to maintain a gradient cooling temperature range of 10° C.

Prior to the 0:45:00 time frame, the setpoint again increases from 30° C. to 37° C. Now the patient temperature is below the setpoint temperature, so the system 10 starts to warm the circulating water. The graph shows the results of the controller 26 warming the circulating water, initially toward a temperature of 40° C. This again corresponds to the gradient 10° C. setting, which corresponds to a circulating water temperature which is 10° higher than the sensed patient temperature of 30° C. Thereafter, the patient's temperature increases in step-like fashion, due to the warming effect of the water, and the controller subsequently increases the temperature of the circulating water, in order to maintain the warming temperature gradient of 10° C. But again, because the system 10 limits the upper temperature of the circulating water to 42° C., the temperature gradient between the circulating water and the patient temperature actually becomes something less than the predetermined temperature magnitude of 10° C. Eventually, at the time of 1:10:0, the patient temperature reaches the setpoint temperature. At that point, the system 10 discontinues warming the circulating water, so that it gradually decreases in temperature to a temperature below the setpoint temperature, after the 1:20:00 time.

The patient's temperature rises again at the 1:25:0 time, and the graph shows a corresponding cooling of the circulating water to the predetermined (or pre-set) cooling temperature gradient of 10° C.

FIG. 3C shows that there are situations when the actual applied gradient warming temperature is not the same as the predetermined temperature gradient. This is because the system 10 automatically maxes out, or limits, the warming of the circulating water to a temperature of 42° C., due to temperature safety override, for high temperatures.

Figure 2:
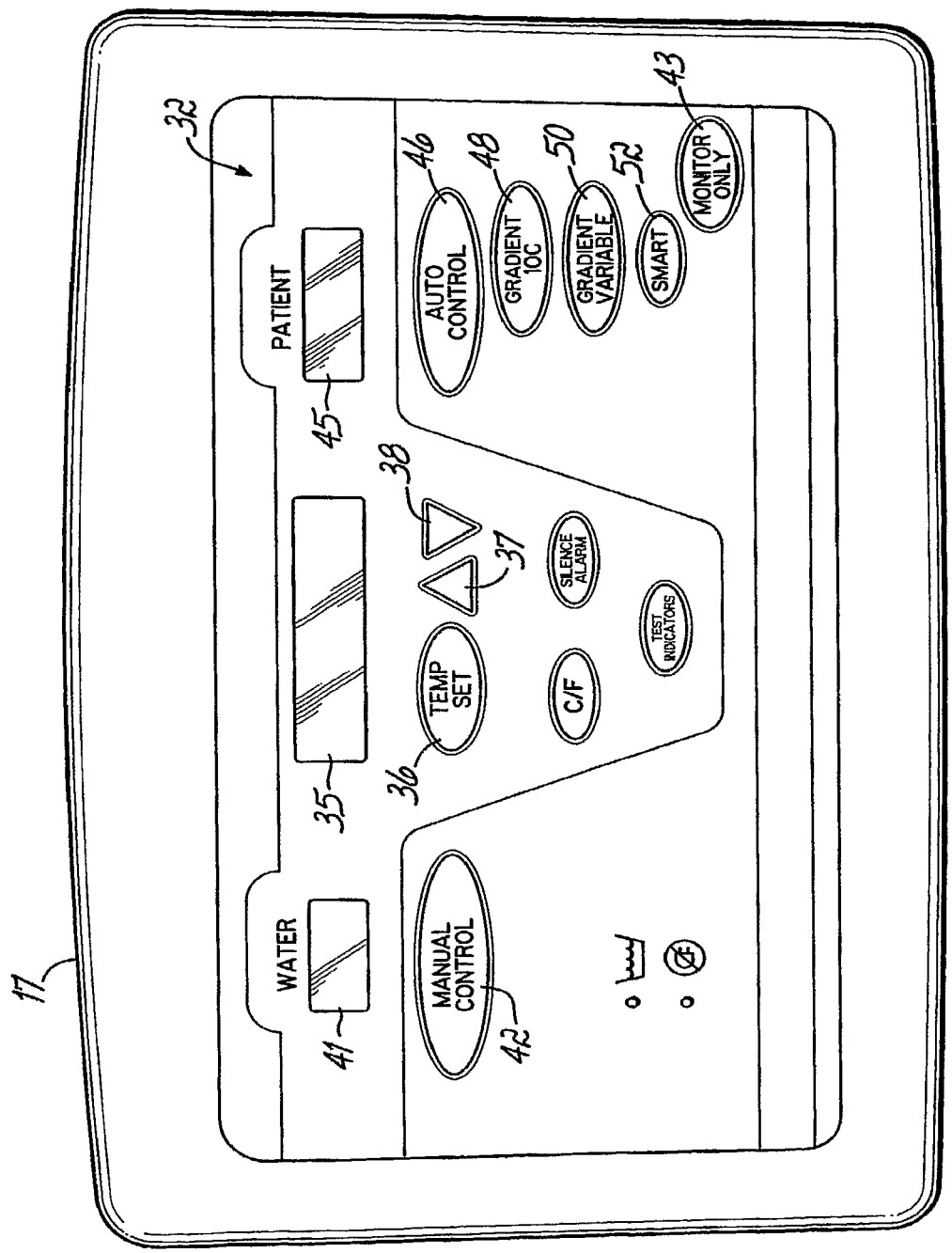
FIG. 2 is a plan view of a control panel of a patient temperature control system according to the present invention.

FIG. 3D is entitled Gradient Variable. It generally shows the same sequence of operating parameters as FIG. 3C, and with similar results, but with a selected predetermined temperature gradient of 3° C., rather than 10° C. This is achieved by push button 50, as shown in FIG. 2. Because of this lower temperature gradient, FIG. 3D shows an initial warming situation where the temperature of the circulating water does not max out at the uppermost limit of 42° C. FIG. 3D shows that this lower temperature gradient also causes step-like decreasing of the patient temperature on the left side of the graph (in three steps), and subsequent thereto, step-like increasing of the patient's temperature on the right side of the graph (in three steps), all in increments of 3° C., followed by one temperature spike at 2:17:34, which then causes the system 10 to cool the circulating water. It is believed that this selectability to the initial temperature gradient will help to reduce the incidents of and magnitude of overshoot conditions.

Notably, in each of FIGS. 3A, 3B, 3C, and 3D, broken line 59 showing the temperature of the B-III water starts in the range of about 19-21° C., a temperature range that is relatively close to room temperature. Thus, during the initial stage of treatment, the temperature of the B-III water (as reflected by line 59), is moving from about room temperature toward the setpoint temperature because of the gradient setting (either 10° C. or another user-selected temperature gradient). From a functional standpoint, the controller 26 causes the temperature of the B-III water to gradually move toward the setpoint temperature, with the user-selected gradient serving as the maximum temperature differential, as measured from the patient's sensed temperature. In use, due to inertia in the water temperature the actual temperature of the B-III water may never attain the particular temperature difference established by the gradient setting.

On the time axis, the numbered intervals are set at six minutes apart in FIG. 3D, wherein the intervals are set at five minutes apart in FIG. 3C.

The Variable Gradient Feature

FIGS. 3E, 3F, 3G, and 3H show the advantageous aspects of the variable gradient feature of the present invention, according to the GRADIENT 10° C. option in combination with the SMART feature. This is done by pushing the SMART push button 52, after activating the GRADIENT 10° C. push button 48. To distinguish among these Figures, the next four subheadings refer to the starting temperature of the circulating water. For each of the situations reflected by these graphs, the initial temperature gradient is 10° C.

Circulating Water Starts at 27° C.

Figure 3E:
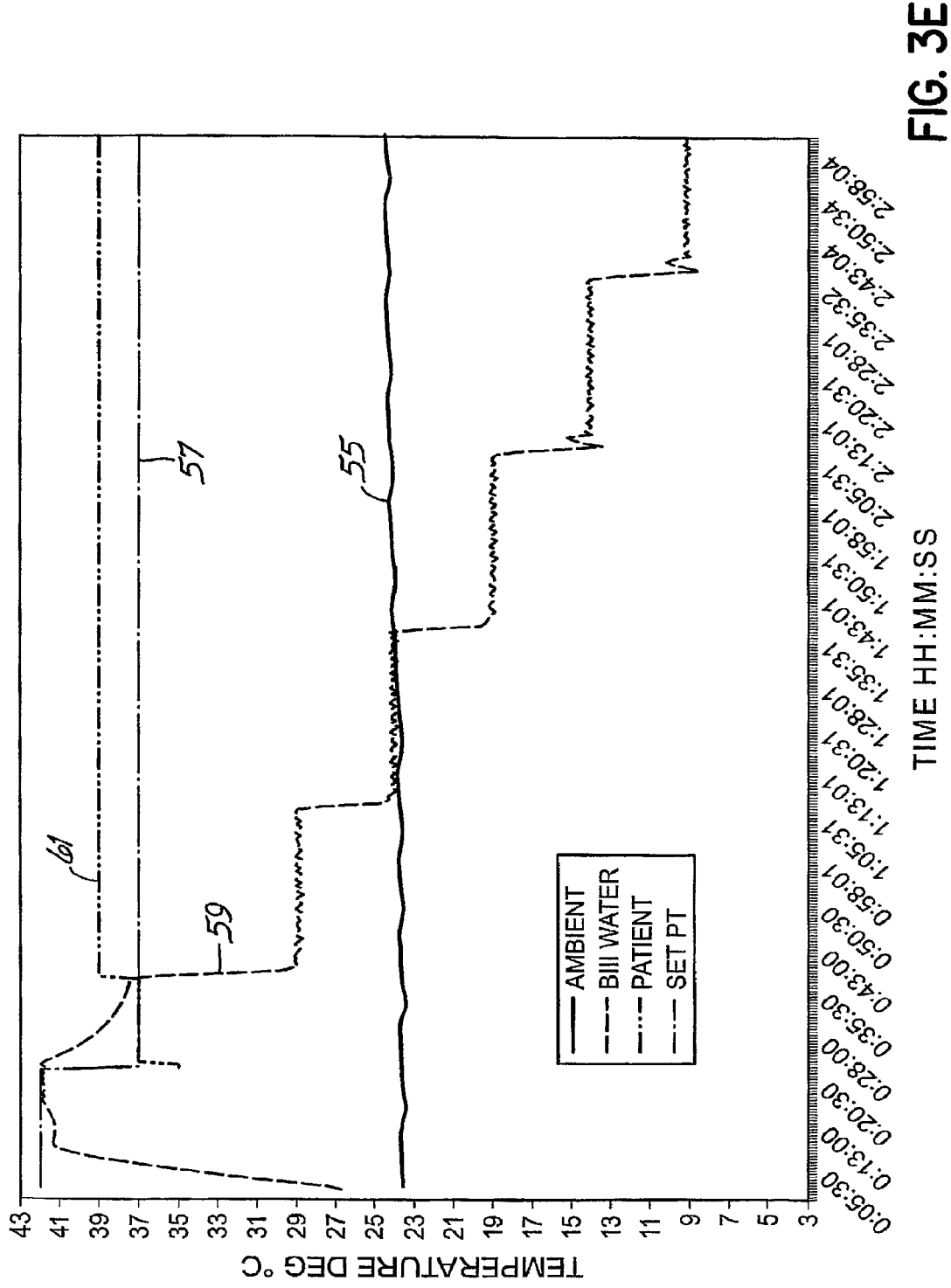

In FIG. 3E, ambient temperature is shown by solid line 55, the setpoint temperature is shown by dashed line 57, the circulating water temperature is shown by dotted line 59, and patient temperature is shown by hybrid line 61. The temperature of the circulating water, on the left, starts at 27° C., above the ambient temperature of 23° C. It appears that the system 10 is actually operating in AUTOMATIC mode until 0:20:30. At that time, the patient temperature first appears on the graph, at 35° C. Because the patient's temperature at that point is below the setpoint temperature of 37° C. (and which decreased from 42° C. at the same time of 0:20:30), the temperature of the circulating water decreases.

At the time 0:35:30, the patient's temperature increases to 39° C., which is two degrees above the setpoint temperature of 37° C. At that point, the controller 26 operates to cool the circulating water to a temperature of 29° C., which is 10° C. below the patient's temperature of 39° C., thus using the initial 10° C. temperature gradient for patient cooling. Thereafter, this graph shows subsequent incremental increases in the cooling gradient temperature, resulting in a 15° gradient at 1:05:31, then a 20° gradient at 1:35:31, then a 25° temperature gradient at 2:05:31, and then a 30° temperature gradient at 2:35:32. Looking at the top of the graph, the patient's temperature has remained flat at 39° C., while the setpoint temperature has remained flat at 37° C. Thus, even though these two temperature lines have remained parallel, or flat, the system 10 periodically (in this case every half hour) incrementally increases the gradient temperature for cooling, in 5° increments, to magnify the efforts to reduce the temperature of the patient to the setpoint temperature. This graph provides a good depiction of variable temperature gradient cooling, wherein the system 10 senses the need to incrementally increase the cooling temperature gradient four times in a row, and in each case, a half hour after the previous incremental increase.

Circulating Water Starts at 9° C.

Figure 3F:
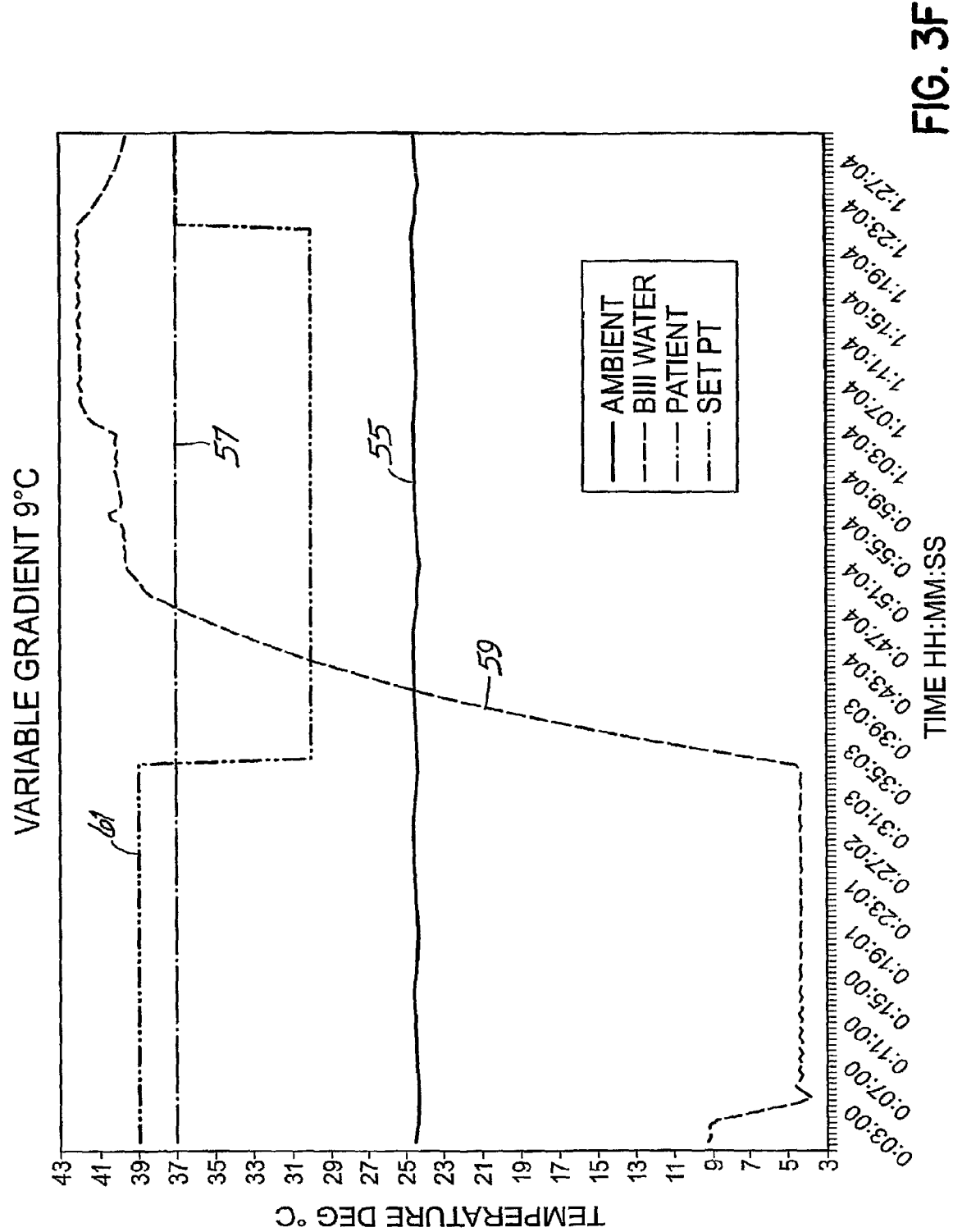

FIG. 3F is a graph which shows a continuation of the situation which occurred at the end (the right side) of FIG. 3E. That is, ambient temperature is still at 24° C., the setpoint temperature is still at 37° C., (where it remains for the duration of the graph) and the patient's temperature, beginning at the left side of the graph, is at 39° C.

If this graph is viewed as a continuation of the previous graph (FIG. 3E), it is seen that at 0:03:00, the system 10 further increases the cooling temperature gradient by another increment of 5° C., to a cooling temperature gradient of about 35° C., with the cooling circulating water cat a temperature of 4° C. Stated another way, the cooling temperature gradient has moved, in incremental step-like fashion, to a value of 35° C. In this case, the system 10 has "bottomed-out," because the cooling temperature gradient cannot reduce any further below 4° C. In this example, 4° C. represents the lower limit for the temperature of the circulating water, for safety reasons, just as 42° C. represents the upper limit temperature for the circulating water.

At 0:35:03, the patient's temperature drops to 30° C., which is 7° C. below the setpoint temperature of 37° C. Thus, the controller 26 recognizes that the patient's temperature needs to be warmed, to increase it to the setpoint of 37° C. This results in heating of, and a steep increase in, the temperature of the circulating water, an increase that continues until about 0:51:04, when the initial warming temperature gradient of 10° C. is reached. Thereafter, at 1:03:04, the system 10 further incrementally increases the warming temperature gradient, in an effort to warm the patient to the setpoint temperature, but the temperature of the circulating water maxes out at 42° C. The patient's temperature eventually rises to the setpoint at the 1:23:04 time.

While this chart (FIG. 3F) may represent a continuation of the temperature situation reflected in the prior graph (FIG. 3E), it should be recognized that the time scales of both graphs are different. Also, as noted previously, these graphs represent computer modeling of the system 10, as presently configured. They do not represent actual patient treatment situations.

Circulating Water Temperature Starts at 22° C.

Figure 3G:
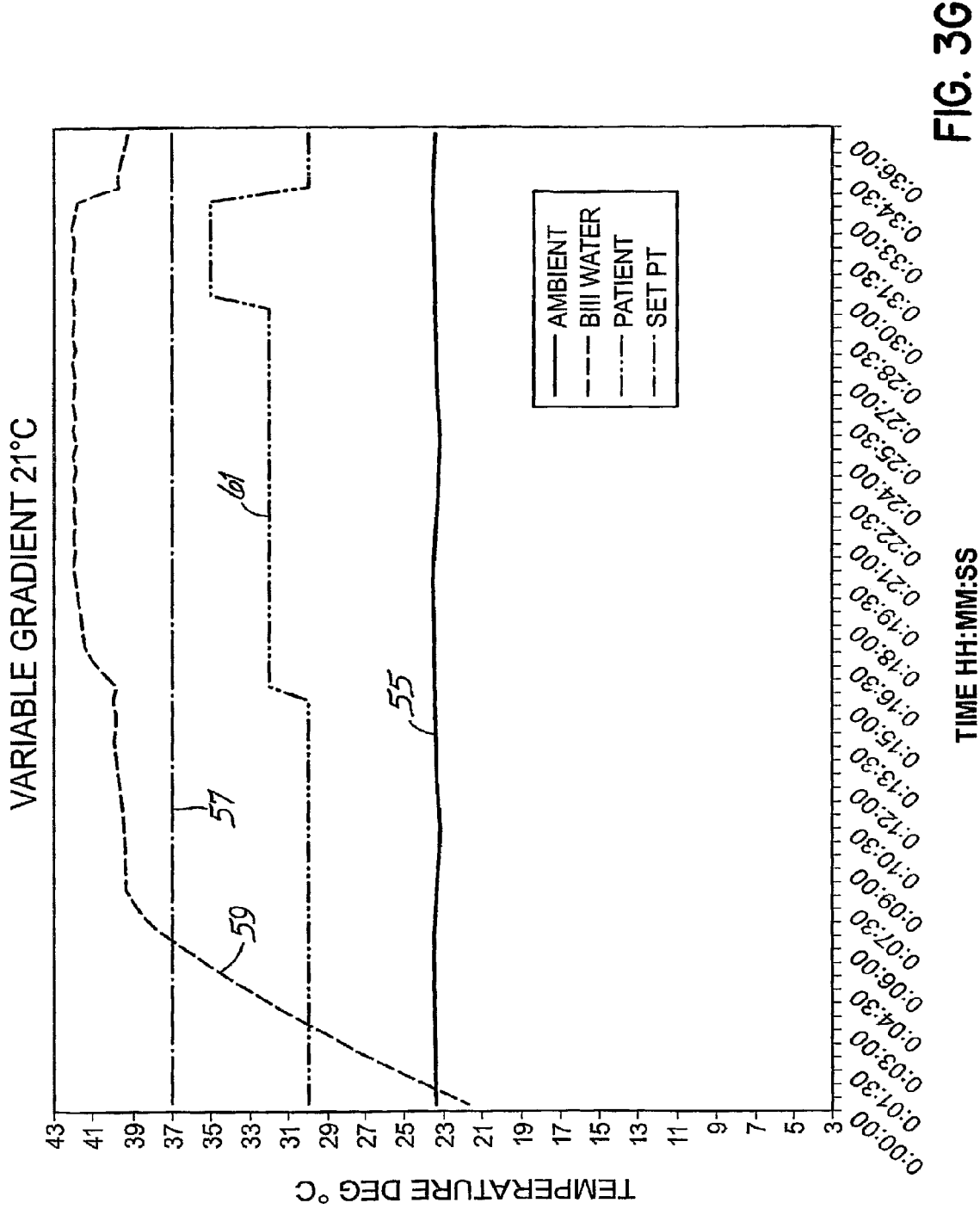

In FIG. 3G, ambient temperature is at 23° C., circulating water temperature starts at about 22° C. below ambient temperature, the patient temperature is shown at 30° C., and the setpoint temperature is shown at 37° C. Under this set of conditions, the system 10 warms the circulating water to raise the patient's temperature to the setpoint temperature. Accordingly, the temperature of the circulating water gradually increases. At the time 0:07:30, the system holds the raised circulating water temperature to a predetermined warming temperature gradient of 10° C. At 0:15:00, the patient's temperature increases from 30° C. to 32° C. Correspondingly, the controller 26 causes an increase in the temperature of the circulating water to 42° C., to maintain the 10° warming temperature gradient. Thereafter, at 0:30:00, the patient's temperature further increases from 32° C. to 35° C. However, because the system 10 has already maxed out with the warmest temperature water allowed, at 42° C., there is no further increase in the gradient temperature. At 00:34:30, the patient's temperature decreases from 35° C. to 30° C. Correspondingly, the controller 26 reduces the temperature of the circulating water to the predetermined 10° temperature gradient, in an effort to warm the patient to the setpoint temperature of 37° C.

Circulating Water Starts at 36° C.

Figure 3H:
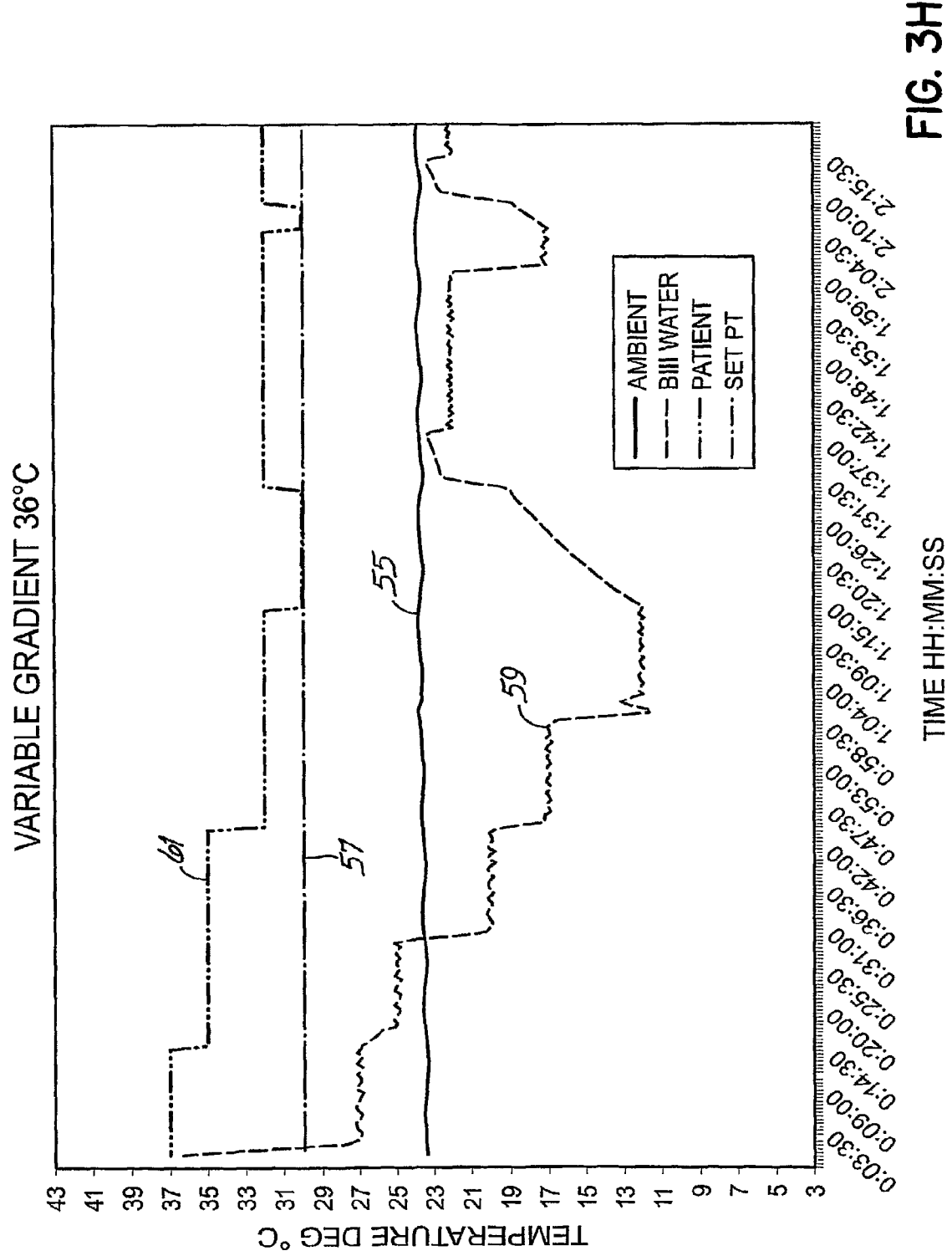

In FIG. 3H, the ambient temperature is shown at 23° C. The setpoint temperature is shown at 30° C., and it remains at 30° C. throughout the entire graph. The patient's temperature is shown at 37° C. The circulating water starts at 36° C.

Because the patient's temperature is initially warmer than the setpoint temperature, the system cools the circulating water, down to 27° C., or 10° lower than the sensed patient temperature of 37° C., corresponding to the initial 10° cooling temperature gradient. At time 00:14:30, the patient's temperature decreases from 37° C. to 35° C., and the system correspondingly cools the circulating water from 27° C. down to 25° C., thereby to retain and maintain the initial 10° cooling temperature gradient. At 00:31:00 (or about 16:30 thereafter), the system has recognized that the 10° cooling temperature gradient is insufficient to cool the patient's temperature down to the setpoint. Therefore, at that point, the system 10 automatically incrementally responds by increasing the temperature gradient by 5° C., to a varied temperature gradient of 15° C. Or stated another way, the system 10 reduces the temperature of the circulating water from 25° C. to 20° C. At time 00:47:30, the patient's temperature decreases from 35° C. to 32° C. Correspondingly, the system 10 reduces the temperature of the circulating water from 20° C. to 17° C. to maintain the 15° temperature differential. At time 1:04:00 (or about 16:30 later), the system 10 again incrementally increases the cooling gradient temperature, to a gradient of 20° C., by reducing the temperature of the circulating water from 17° C. down to 12° C., in an effort to reduce the patient's temperature down to the setpoint temperature of 30° C. At time 1:15:00, the patient's temperature reduces to 30° C., the setpoint temperature. This causes the system to discontinue cooling of the circulating water, thereby allowing the temperature of the cooling water to gradually raise to the ambient temperature. At 1:31:30, the patient's temperature raises from 30° C. to 32° C. Correspondingly, the system 10 cools the circulating water to achieve a 10° cooling gradient temperature. At time 2:04:30, the system 10 determines that the initial 10° gradient temperature has not been sufficient to cool the patient down to the setpoint temperature, so the system 10 causes an incremental increase in the gradient temperature by 5° C., to 15° C. Or stated another way, the system 10 lowers the temperature of the circulating water from 22° C. down to 17° C. At time 2:10:00, the patient's temperature again reduces to the setpoint temperature, whereupon the controller discontinues cooling the circulating water. Thereafter, the temperature of the circulating water gradually raises toward ambient. But soon afterwards, the patient's temperature again increases to 32° C., and then the system 10 initiates cooling of the circulating water toward the 10° temperature gradient.

Variable Gradient (Initial Gradient of 4° C., Not 10° C.)

Figure 3I:
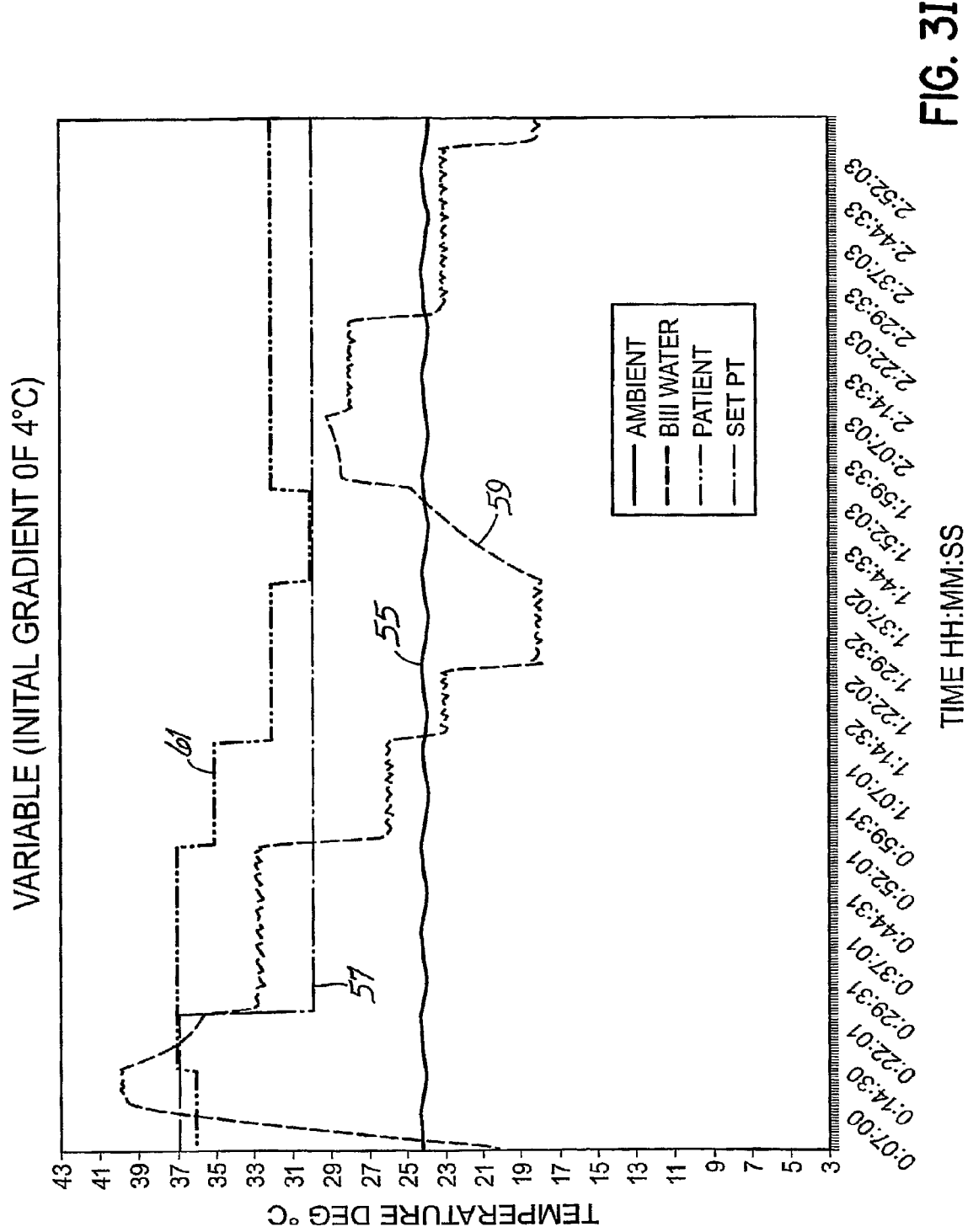

FIG. 3I shows ambient temperature at 24° C., circulating water initially at 20° C., patient temperature initially at 36° C., and setpoint temperature initially at 37° C. To achieve this example, the operator chooses the SMART feature (push button 52) after selecting the GRADIENT VARIABLE of 4° C. (push button 48).

With a sensed patient temperature lower than the setpoint (as shown at the left side of the graph), the controller 26 heats the circulating water to an initial warming temperature gradient of 4° C., at 0:14:30. This causes the patient's temperature to increase to the setpoint, and thereafter, the controller 26 correspondingly discontinues further heating of the circulating water.

At 0:29:31, the setpoint temperature decreases from 37° C. to 30° C. Then the sensed patient temperature is greater than the setpoint temperature, so the system 10 operates to cool the circulating water to reduce the patient's temperature, first via the initial temperature gradient of 4° C.

At a time of 0:59:31, the system 10 determines that the patient temperature has not yet lowered to the setpoint temperature. Therefore, the system 10 increases the magnitude of the temperature gradient, from 4° C. to 9° C., so that the circulating water is now 26° C., or 9° C. below the patient temperature of 35° C. Thus, the system 10 incrementally increases the gradient temperature by 5° C., from 4° C. to 9° C. Even though the patient temperature then steps down to 32° C., at 1:14:32, the system 10 initially maintains this 9° C. temperature gradient. Thereafter, at a time of 1:22:02 (about 7:30 later), the system 10 further determines that the patient's temperature has not lowered fast enough. Therefore, the system 10 further reduces the temperature of the circulating water to a temperature differential which is now 14° C. below the patient's temperature, or to a temperature of 18° C., compared to a patient temperature of 32° C. In other words, the controller 26 has increased the magnitude of the cooling temperature gradient from 9° C. to 14° C., to maintain the temperature of the circulating water at a value of 14° C. below the patient temperature. Eventually, at time 1:37:02, the patient's temperature decreases to the setpoint. At that point, the system 10 discontinues further cooling of the circulating water, and the temperature of the circulating water gradually begins to rise to ambient.

At 1:52:03, the patient temperature again increases above the setpoint. The controller 26 reacts by cooling the circulating water to the selected 4° C. initial temperature differential, as shown from time frame 2:07:03 to 2:22:03. However, at that time, i.e., 2:22:03, the controller 26 determines that the patient temperature has not reduced to the setpoint. Accordingly, the controller 26 further increases the magnitude of the 4° C. gradient to a 9° C. gradient, to provide a greater magnitude of cooling to the patient. Thereafter, at the right edge of the graph, the controller 26 again determines that the patient's temperature has not reduced to the setpoint (or to an acceptable range near the setpoint). Therefore, the controller 26 again reduces the temperature of the circulating water, or stated another way, increases the magnitude of the temperature differential by another increment of 5° C., from 9° C. to 14° C. Thus, the controller 26 increases or decreases the temperature gradient, in increments of 5° C., depending on the subsequently sensed patient temperature.

With the present invention, the temperature can be sensed continuously, or intermittently. Also, a time interval may be selectable for determining when it is necessary to vary the temperature gradient. Nonetheless, a time interval of 30 minutes seems to be preferable. Also, the SMART feature can be selected after the fact, that is, some time into the patient temperature control treatment. That is done by simply depressing the SMART push button 52, when already in the GRADIENT 10° C., in the GRADIENT VARIABLE mode.

In total, the system provides seven modes of operation, namely: 1) MANUAL CONTROL, 2) AUTO CONTROL, 3) MONITOR ONLY, 4) GRADIENT 10° C., 5) GRADIENT VARIABLE, 6) GRADIENT 10° C./SMART, AND 7) GRADIENT VARIABLE/SMART. It is believed that no other patient temperature control system provides any of the last three of these modes. The prior art described in the background does not teach or suggest any of these last three modes, nor the concept of automatically changing the temperature gradient during treatment, thereby to automatically decrease or increase the temperature gradient depending on subsequently sensed patient temperatures. With respect to the fifth mode, i.e. GRADIENT VARIABLE, neither U.S. Pat. No. 6,517,510 nor the Sarns Manual teaches the ability for a user to select any one of a plurality of different gradient options. To the contrary, with each of these two prior art references the gradient is permanently set at the factory during manufacture, at two fixed differentials. As a result, because of the combination of all of these features, and particularly the SMART modes, the system described herein is capable of achieving a high degree of versatility and user-friendliness in providing cost-effective and comfortable patient temperature control.

This invention has been described in the context of the accompanying Figures, and particularly the graphs. Nonetheless, those skilled in the art will recognize that this system 10, with the variable temperature gradient feature, is susceptible to numerous variations in implementation and modification. In short, this specification is meant to be exemplary, relative to the presently preferred embodiments of the invention, not specific or limiting. Thus, it is to be understood that the invention itself is not limited by this specification, but instead is defined only by reference to the following claims, as understood in the context of this specification.

I claim:

1. A patient temperature control system comprising:
   a) a fluid circuit for conveying warming/cooling fluid to a patient warming/cooling device, the patient warming/cooling device capable of being non-invasively applied to a patient for conductive warming/cooling of the patient according to a hypo-hyperthermia treatment;
   b) a controller operatively connected to the fluid circuit to control the flow and the temperature of the warming/cooling fluid there through;
   c) a first temperature sensor adapted to sense the temperature of the patient and operatively connected to the controller;
   d) a second temperature sensor adapted to sense the temperature of the warming/cooling fluid and operatively connected to the controller;
   e) the controller adapted to warm the warming/cooling fluid being conveyed to the warming/cooling device, thereby to conductively warm the patient in a non-invasive manner when the first sensor senses a patient temperature lower than a selected target temperature;
   f) the controller also operative to cool the warming/cooling fluid being conveyed to the warming/cooling device, thereby to conductively cool the patient in a non-invasive manner when the first sensor senses a patient temperature higher than the selected target temperature;
   g) wherein the controller automatically controls the warming or cooling of the warming/cooling fluid during an initial stage, at a temperature that differs from the sensed patient temperature by, at a maximum, a predetermined initial stage temperature gradient; and
   h) the controller, during a subsequent stage, automatically controls the warming or cooling of the warming/cooling fluid by automatically varying the magnitude of the temperature gradient from the predetermined initial stage temperature gradient toward a subsequent temperature gradient, in response to a subsequently sensed temperature of the patient as sensed via the first sensor, if the sensed patient temperature has not moved sufficiently close to the selected target temperature, thereby to more quickly bring the temperature of the patient to the selected target temperature and to do so in a manner which minimizes overshoot, and wherein the controller does not automatically vary the magnitude of the temperature gradient from the predetermined initial stage temperature gradient if the sensed patient temperature has moved sufficiently close to the selected target temperature.

2. The patient temperature control system of claim 1 wherein the controller causes the subsequent variations in the magnitude of the temperature gradient to occur at specified time intervals.

3. The patient temperature control system of claim 2 wherein the duration of the specified time intervals is selectable.

4. The patient temperature control system of claim 2 wherein the durations of the subsequent specified time intervals remain the same.

5. The patient temperature control system of claim 1 wherein the controller is configured to enable a user to select the magnitude of the predetermined initial stage temperature gradient, from a plurality of predetermined initial stage temperature gradient options.

6. The patient temperature control system of claim 1 wherein the controller is configured such that each of the subsequent variations in the magnitude of the temperature gradient, which result from the subsequently sensed patient temperatures, is at a fixed temperature increment.

7. The patient temperature control system of claim 6 wherein the fixed increment for the subsequent variations in the temperature gradients is about 5° C.

8. The patient temperature control system of claim 1 wherein the patient warming/cooling device is a blanket and the fluid is water.

9. A method of controlling the temperature of a patient using a patient temperature control system, the method comprising conductively warming/cooling the patient in a non-invasive manner via warmed/cooled fluid that flows through a device located near the patient, the warming/cooling fluid being warmed/cooled at a temperature which, at a maximum, differs from the patient's first sensed temperature by a predetermined temperature magnitude; and thereafter, automatically varying said predetermined temperature magnitude if the subsequently sensed patient temperature has not moved sufficiently close to a selected setpoint temperature within a given time window, but maintaining the predetermined temperature magnitude if the subsequently sensed patient temperature has moved sufficiently close to the selected setpoint temperature within the given time window.

10. The method of claim 9 wherein the duration of the given time is selectable.

11. A patient temperature control system comprising:
a blanket;
a controller operatively connected to the blanket for, in a mode of automatic control, conductively warming/cooling a patient in a non-invasive manner via warming/cooling fluid conveyed through the blanket, wherein the warming/cooling fluid is warmed/cooled at a temperature which is based on an initial predeteimined temperature differential relative to the patient's sensed temperature, said initial predetermined temperature differential being user-selectable such that one of at least three different initial predetermined temperature differentials may be selected, and
wherein the controller automatically varies the temperature differential from said initial, user selectable predetermined temperature differential toward a subsequent temperature differential, dependent on the patient's subsequently sensed temperature, if the patient's subsequently sensed temperature has not moved sufficiently close to a selected setpoint temperature within a given time window, but wherein the controller maintains the same temperature differential if the patient's subsequently sensed temperature has moved sufficiently close to the selected setpoint temperature.

* * * * *